United States Patent [19]

Karpf

[11] Patent Number: 4,657,552
[45] Date of Patent: Apr. 14, 1987

[54] PROSTHESIS OF THE HIP

[75] Inventor: Kurt Karpf, Holderbank, Switzerland

[73] Assignee: Emil Schenker AG, Schönenwerd, Switzerland

[21] Appl. No.: 716,834

[22] Filed: Mar. 28, 1985

[30] Foreign Application Priority Data

Apr. 2, 1984 [CH] Switzerland ............ 1656/84

[51] Int. Cl.⁴ ............................................. A61F 2/32
[52] U.S. Cl. ............................................. 623/23
[58] Field of Search ............ 623/21, 22, 23; 128/92 C, 92 CA

[56] References Cited

U.S. PATENT DOCUMENTS

| | | | |
|---|---|---|---|
| 2,719,522 | 10/1955 | Hudack | 623/23 |
| 4,406,023 | 9/1983 | Harris | 128/92 CA |

FOREIGN PATENT DOCUMENTS

| | | | |
|---|---|---|---|
| 0027160 | 4/1981 | European Pat. Off. | 623/23 |
| 2324865 | 11/1974 | Fed. Rep. of Germany | 623/23 |
| 2331728 | 1/1975 | Fed. Rep. of Germany | 623/23 |
| 2805305 | 8/1978 | Fed. Rep. of Germany | 623/23 |
| 2931750 | 2/1981 | Fed. Rep. of Germany | 623/23 |
| 8213101 | 8/1982 | Fed. Rep. of Germany | 623/23 |
| 2493139 | 5/1982 | France | 623/23 |
| 0112423 | 7/1984 | France | 623/23 |
| 2118441 | 11/1983 | United Kingdom | 623/23 |

Primary Examiner—Richard J. Apley
Assistant Examiner—David J. Isabella
Attorney, Agent, or Firm—Peter K. Kontler

[57] ABSTRACT

The stem of the cephalic femoral component of a hip prosthesis is bounded by two pairs of longitudinally extending surfaces including two relatively wide and two relatively narrow surfaces. At least one of the narrow surfaces is convex, all of the surfaces taper in a direction toward a rounded tip of the stem, the radius of curvature of the convex surface or surfaces decreases in a direction toward the tip, and the wider surfaces taper toward each other in a direction from the one toward the other narrower surface. This reduces the likelihood of loosening of the stem in the medullar canal of the femur wherein the stem is implanted without cement, and the bone around the stem is less likely to be subjected to excessive localized stresses.

11 Claims, 4 Drawing Figures

U.S. Patent  Apr. 14, 1987  4,657,552
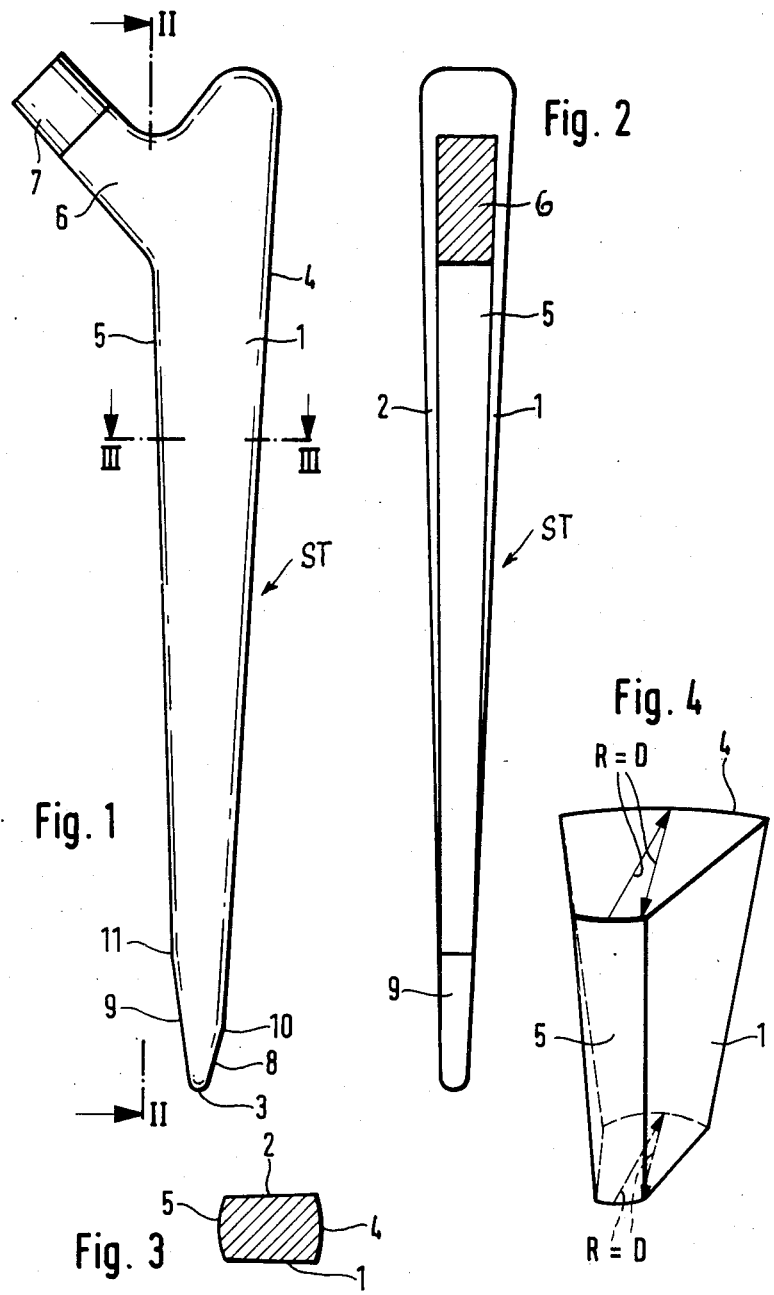

4,657,552

PROSTHESIS OF THE HIP

CROSS-REFERENCE TO RELATED CASE

The commonly owned copending patent application Ser. No. 675,523 filed Nov. 28, 1984 by Kurt Karpf et al. discloses a pneumatic impact tool which can be used to prepare a bone canal for reception of a femoral component embodying the present invention.

BACKGROUND OF THE INVENTION

The present invention relates to hip prostheses in general, and more particularly to improvements in cephalic femoral components of such prostheses.

It is already known to configure the stem (i.e., that part which is implantable in the medullar canal of the femur) of the cephalic femoral component with relatively wide front and rear sides or surfaces which are disposed opposite each other and extend longitudinally of the stem, and with relatively narrow longitudinally extending lateral and medial sides or surfaces which also extend longitudinally of the stem and are disposed opposite each other. Such stem has a substantially rectangular outline and the width of each of the four surfaces decreases in a direction toward a rounded tip which is distal from the hip when the stem is implanted in the medullar canal of the femur. That end portion of the stem which is remote from the tip has a laterally extending neck or arm which serves to carry the ball, i.e., the male component of the hip joint which can be received in the cotyloid compartment of the hip prosthesis. The stem acts not unlike a wedge and is supposed to fit snugly into and to remain tight in the medullar canal of the femur. Such stem can be implanted with or without cementing subsequent to adequate preparation of the medullar canal. If the implantation is to take place without the use of a cement, that end portion of the stem which includes the rounded tip must constitute a wedge. Also, the width of that portion of the medial surface of the stem which is remote from the tip must increase arcuately in order to conform the outline of the shank to the shape of the adjacent portion of the femur in the calcar region. The corresponding part of the stem bears against the femur and, in the absence of highly accurate preparation of the medullar canal, can adversely influence the action of the conical supporting member for the ball fitting into the cotyloid portion of the prosthesis at that end of the stem which is remote from the rounded tip. This can result in loosening of the stem and hence in the need for remedial surgery in order to restore the operability of the artificial hip joint.

Furthermore, the very pronounced stresses which develop when a person using the just described cephalic femoral component is walking or running must be uniformly distributed to various portions of the femur, i.e., the stem and the femur should be in extensive surface-to-surface contact with one another in order to avoid deterioration of the femur as a result of excessive localized stressing of the bone tissue.

OBJECTS AND SUMMARY OF THE INVENTION

An object of the present invention is to provide a novel and improved cephalic femoral component which can be used in a prosthesis of the hip and which is constructed and configurated in such a way that it is not likely to become loose in the medullar canal of the femur even if the magnitude of stresses which the femoral component takes up and/or transmits during walking, jogging or running varies within a very wide range.

Another object of the invention is to provide a cephalic femoral component which is in large surface-to-surface contact with the adjacent portions of the femur.

An additional object of the invention is to provide a cephalic femoral component which can be implanted without the use of cement.

Still another object of the invention is to provide a novel and improved hip prosthesis which employs the above outlined femoral component.

A further object of the invention is to provide the femoral component with a novel and improved shank that fits into the medullar canal or recess of the femur.

The invention resides in the provision of a cephalic femoral component which forms part of a hip prosthesis and comprises an elongated stem which is implantable in the medullar canal of the femur. The stem has relatively wide longitudinally extending front and rear surfaces which are disposed opposite each other, and relatively narrow longitudinally extending lateral and medial surfaces which are also disposed opposite each other. The cross-sectional outline of the stem is preferably a rectangle and the stem comprises a rounded tip which is remote from the hip when the stem is implanted in the medullar canal of the femur. The width of each of the aforementioned surfaces decreases in a direction toward the tip and at least one of the lateral and medial surfaces has a convex outline with a radius of curvature which decreases gradually in a direction toward the tip. Alternatively, or in addition to the just outlined configuration and mutual orientation of the lateral and medial surfaces, the front and rear surfaces of the stem can be disposed in two mutually inclined planes which converge or taper toward each other in a direction toward the tip. The width of the medial surface is preferably less than the width of the lateral surface, and the femoral component further comprises an arm or neck which extends from the medial surface at a location remote from the tip of the stem and has means (e.g., a conical member) for supporting the ball that fits into the cotyloid portion of the prosthesis.

The radius of curvature of the convex (lateral and/or medial) surface in each of a plurality of planes which are normal to the stem at least approximates the distance between the medial and lateral surfaces in the respective plane.

Each of the medial and lateral surfaces preferably includes a relatively long first portion which is more distant from the tip of the shank and a relatively short second portion which is adjacent to the tip and makes with the respective first portion an obtuse angle slightly smaller than 180°. The length of the second portion of the medial surface preferably exceeds the length of the second portion of the lateral surface as considered in the longitudinal direction of the stem. The first portion of the lateral and/or medial surface is at least substantially straight. The medial and lateral surfaces can be inclined relative to and can taper toward each other in a direction toward the tip at an angle of between about 5° and 10° (preferably substantially or exactly 5°).

In accordance with an additional feature of the invention, the front and rear surfaces converge toward each other in a direction from one of the lateral and medial surfaces toward the other of the lateral and medial surfaces. Thus, the front and rear surfaces can converge toward each other in a first direction toward the tip of the stem as well as in a second direction transversely of the first direction (preferably from the lateral surface toward the narrower medial surface). This also contributes to more reliable retention of the stem in the medullar canal of the femur regardless of whether the stem is implanted with or without the use of a suitable cement.

The novel features which are considered as characteristic of the invention are set forth in particular in the appended claims. The improved femoral component itself, however, both as to its construction and the mode of shaping and implanting the same, together with additional features and advantages thereof, will be best understood upon perusal of the following detailed description of certain specific embodiments with reference to the accompanying drawing.

BRIEF DESCRIPTION OF THE DRAWING

FIG. 1 is a schematic elevational view of a cephalic femoral component which embodies the invention;

FIG. 2 is a partly sectional view as seen in the direction of arrows from the line II—II of FIG. 1;

FIG. 3 is a sectional view as seen in the direction of arrows from the line III—III of FIG. 1; and FIG. 4 is an enlarged fragmentary perspective view of an intermediate portion of the stem forming part of the femoral component which is shown in FIGS. 1 to 3.

DESCRIPTION OF THE PREFERRED EMBODIMENTS

FIGS. 1 to 4 show a cephalic femoral component which can form part of a total hip prosthesis and includes an elongated stem ST made of a suitable metallic or plastic material and having a substantially rectangular cross-sectional outline (see FIG. 3). That end portion of the stem ST which is remote from the hip joint when the stem is implanted in the medullar recess or canal of the femur (not shown) is formed with a rounded tip 3, and the stem ST comprises two relatively wide (front and rear) sides or surfaces 1, 2 which extend longitudinally of the stem, which are disposed opposite each other, and whose width decreases in a direction toward the tip 3. The stem ST further comprises two relatively narrow (lateral and medial) sides or surfaces 4, 5 which are also disposed opposite each other, which also extend longitudinally of the stem, and whose width also decreases in a direction toward the tip 3.

That portion of the medial surface 5 which is remote from the tip 3 has an outwardly extending arm or neck 6 provided with a ball supporting means 7 in the form of a conical member receivable in a ball that fits into the catyloid portion or component (not shown) of the hip prosthesis. The neck or arm 6 and the stem ST make a relatively large obtuse angle.

Due to the aforediscussed reduction of the width of the surfaces 1, 2, 4 and 5 in a direction toward the tip 3, the stem ST acts not unlike a twin wedge so that it can be firmly lodged in the femur in two mutually inclined directions in response to implantation that follows an adequate preparation of the medullar canal for reception of the stem.

If the medullar canal is not prepared with a very high degree of accuracy, only the surfaces 1, 2 or only the surfaces 4, 5 are likely to be wedged into the femur. This can result in the possibility of loosening of the stem ST in the canal in the regions of those surfaces (1, 2 or 4, 5) which are not in intimate or pronounced contact with the adjacent portions of the femur. In accordance with a feature of the invention, the likelihood of such loosening is eliminated or greatly reduced in that at least one of the surfaces 4, 5 is a convex surface (the convexity of both such surfaces can be readily seen in FIGS. 3 and 4). The surfaces 4 and 5 serve primarily for the transmission of forces and their radii of curvature decrease in a direction toward the tip 3 of the stem ST. Moreover, the radius (R) of curvature of each of the surfaces 4, 5 (or of the surface 4 or 5 if only one of these surfaces is a convex surface) preferably equals or approximates the distance (D) between the surfaces 4 and 5 in any one of a plurality of planes which extend transversely of and intersect the stem ST. Two such planes are the planes of the upper and lower end faces of the fragment of the stem ST which is shown in FIG. 4. It will be noted that the width of the medial surface 5 is less than the width of the lateral surface 4.

In addition to or in lieu of the just outlined configuration and orientation of the surfaces 4 and 5, the surfaces 1 and 2 are preferably inclined relative to each other and converge toward one another in a direction toward the tip 3. This can be readily seen in FIG. 2. Such undertaking also reduces the likelihood of loosening of the implanted stem ST in the medullar canal of the femur. Moreover, the surfaces 1 and 2 converge toward each other in a direction from the lateral surface 4 toward the narrower medial surface 5.

In order to avoid the development of excessive local stresses between the implanted stem ST and the femur, each of the surfaces 4 and 5 preferably includes a relatively long first portion which is remote from the tip 3 and a relatively short second portion (8, 9) which makes with the respective first portion a large obtuse angle. The second portion 9 of the medial surface 5 is longer than the second portion 8 of the lateral surface 4, i.e., the line 11 where the two portions of the medial surface 5 meet is more distant from the tip 3 than the line 10 where the second portion 8 of the lateral surface 4 merges into the first portion of such surface. Thus, the second portions 8, 9 of the surfaces 4 and 5 bound a rather pronounced wedge which begins at the lines 10, 11 and ends at the tip 3.

The just discussed configuration of the surfaces 4 and 5 reduces the likelihood of development of so-called annular or circumferential stresses in the tubular portion of the femur which surrounds the medullar canal for the stem ST. Thus, the inherently elastic bone material around the stem ST is not subjected to excessive stresses in one or more planes which extend transversely of the implanted stem. This reduces the likelihood of bone fractures as a result of the development of circumferential stresses. Moreover, the mutually inclined portions 8, 9 of the surfaces 4 and 5 facilitate the implantation of the shaft ST in the femur.

In order to prevent the stem ST from bearing against the femur in the calcar region, at least one of the surfaces 4 and 5 (especially the surface 4) is straight. This can be readily seen in the upper portion of FIG. 1 wherein the first portions of surfaces 4 and 5 are straight all the way from the upper end portion of the stem ST to the lines 10 and 11.

The convex configuration of the lateral and medial surfaces 4 and 5 also reduces the likelihood of development of localized peaks of stresses between the stem ST and the femur. The angle between the surfaces 4 and 5 can be between about 5° and 10°, preferably close to or exactly 5°. The obtuse angle between the two portions of the lateral surface 4 can be in the range of between about 165° and 170°, and the angle between the two portions of the medial surface 5 can be between about 170° and 175°. The angle at which the surfaces 1 and 2 converge toward each other in a direction from the lateral surface 4 toward the medial surface 5 can be about 4°, and the angle between the surfaces 1 and 2 in a direction toward the tip 3 can be in the range of between about 2° and 3°.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. In a hip prosthesis, a cephalic femoral component comprising an elongated stem which is implantable in the medullar canal of the femur and has a relatively wide longitudinally extending front and rear surfaces which are disposed opposite each other and relatively narrow longitudinally extending lateral and medial surfaces which are disposed opposite each other, said stem having a rounded tip which is distal from the hip when the stem is implanted in the medullar canal and the width of said front and rear surfaces decreasing in a direction toward said tip, at least one of said lateral and medial surfaces having a convex outline and the radius of curvature of said one surface in each of a plurality of planes which extend transversely to the longitudinal axis of said stem at least approximating the shortest distance between said one surface and that point of the other of said lateral and medial surfaces which is located in the respective plane substantially midway between said front and rear surfaces, the radius of curvature of said one surface decreasing in a direction toward said tip.

2. The femoral component of claim 1, wherein said front and rear surfaces are disposed in two mutually inclined planes which converge toward each other in a direction toward said tip and the radius of curvature of said one surface decreases gradually in a direction toward said tip.

3. The femoral component of claim 1, wherein each of said medial and lateral surfaces includes a first portion more distant from and a second portion adjacent to said tip each of said second portions making an obtuse angle with the respective first portion.

4. The femoral component of claim 3, wherein the length of the second portion of said medial surface exceeds the length of the second portion of said lateral surface, as considered in the longitudinal direction of said stem.

5. The femoral component of claim 3, wherein the second portion of at least one of said lateral and medial surfaces is at least substantially straight.

6. The femoral component of claim 1, wherein said medial and lateral surfaces are inclined relative to and taper toward each other in a direction toward said tip and make an angle of between about 5 and 10 degrees.

7. The femoral component of claim 6, wherein said angle equals or approximates 5 degrees.

8. The femoral component of claim 1, wherein said stem has a substantially rectangular cross-sectional outline.

9. The femoral component of claim 1, wherein the width of said medial surface is less than the width of said lateral surface, as considered transversely of said stem.

10. The femoral component of claim 1, further comprising an arm extending from said medial surface at a location remote from said tip, said arm having means for supporting the ball that fits into the cotyloid portion of the prosthesis.

11. The femoral component of claim 10, wherein said supporting means includes a conical member.

* * * * *